US009535005B2

(12) United States Patent
Page et al.

(10) Patent No.: US 9,535,005 B2
(45) Date of Patent: Jan. 3, 2017

(54) ELECTRO-OPTIC GRATING-COUPLED SURFACE PLASMON RESONANCE (EOSPR)

(71) Applicant: Ciencia, Inc., East Hartford, CT (US)

(72) Inventors: William Page, Storrs, CT (US); George N. Gibson, Storrs, CT (US); Ernest F. Guignon, Canton, CT (US)

(73) Assignee: Ciencia, Inc., East Hartford, CT (US)

( * ) Notice: Subject to any disclaimer, the term of this patent is extended or adjusted under 35 U.S.C. 154(b) by 0 days.

(21) Appl. No.: 15/200,217

(22) Filed: Jul. 1, 2016

(65) Prior Publication Data

US 2016/0313247 A1    Oct. 27, 2016

Related U.S. Application Data

(63) Continuation of application No. 14/534,511, filed on Nov. 6, 2014, now Pat. No. 9,383,312.

(60) Provisional application No. 61/900,548, filed on Nov. 6, 2013.

(51) Int. Cl.
   *G01N 21/00*     (2006.01)
   *G01N 21/552*    (2014.01)
   *G02F 1/19*      (2006.01)

(52) U.S. Cl.
   CPC ............ *G01N 21/553* (2013.01); *G02F 1/195* (2013.01)

(58) Field of Classification Search
   CPC ............ G01N 33/54373; G01N 21/274; G01N 21/6452; G01N 35/028; G01N 33/54313; G01N 21/31; G01N 21/636; G01N 2333/726; G01N 2458/00; G01N 2500/02;G01N 2500/04; G01N 33/5308; G01N 33/56966
   See application file for complete search history.

(56) References Cited

U.S. PATENT DOCUMENTS

| | | | | |
|---|---|---|---|---|
| 5,856,873 A | * | 1/1999 | Naya | G01N 21/211 356/369 |
| 6,239,876 B1 | * | 5/2001 | Brandenberg | G01N 21/45 356/481 |
| 6,982,819 B2 | * | 1/2006 | Sawin | B82Y 20/00 359/245 |
| 7,057,786 B2 | * | 6/2006 | Sawin | B82Y 20/00 345/87 |
| 2002/0009812 A1 | * | 1/2002 | Miura | G01N 21/553 436/518 |

(Continued)

*Primary Examiner* — Michael P Stafira
(74) *Attorney, Agent, or Firm* — Alix, Yale & Ristas, LLP

(57) ABSTRACT

An instrument for measuring and analyzing surface plasmon resonance (SPR) and/or surface plasmon coupled emission on an electro-optic grating-coupled sensor surface is described herein. The sensor chip achieves SPR through a grating-coupled approach, with variations in the local dielectric constant at regions of interest (ROI) at the sensor surface detected as a function of the intensity of light reflecting from these ROI. Unlike other grating-based approaches, the metal surface is sufficiently thin that resonant conditions are sensitive to dielectric constant changes both above and below the metal surface (like the Kretschmann configuration). Dielectric constant shifts that occur as mass accumulates on the surface can be returned to reference intensities by applying voltage across the underlying electro-optic polymer. Approaches to the development of the sensor surfaces are described, as are software and hardware features facilitating sample handling, data gathering, and data analysis by this solid-state approach.

6 Claims, 2 Drawing Sheets

(56) References Cited

U.S. PATENT DOCUMENTS

| | | | |
|---|---|---|---|
| 2003/0206708 A1* | 11/2003 | Estes | B82Y 20/00 385/130 |
| 2005/0248829 A1* | 11/2005 | Sawin | B82Y 20/00 359/321 |
| 2008/0062418 A1* | 3/2008 | Magnusson | G01N 21/253 356/307 |
| 2012/0286163 A1* | 11/2012 | Stiens | G02F 1/195 250/340 |

* cited by examiner

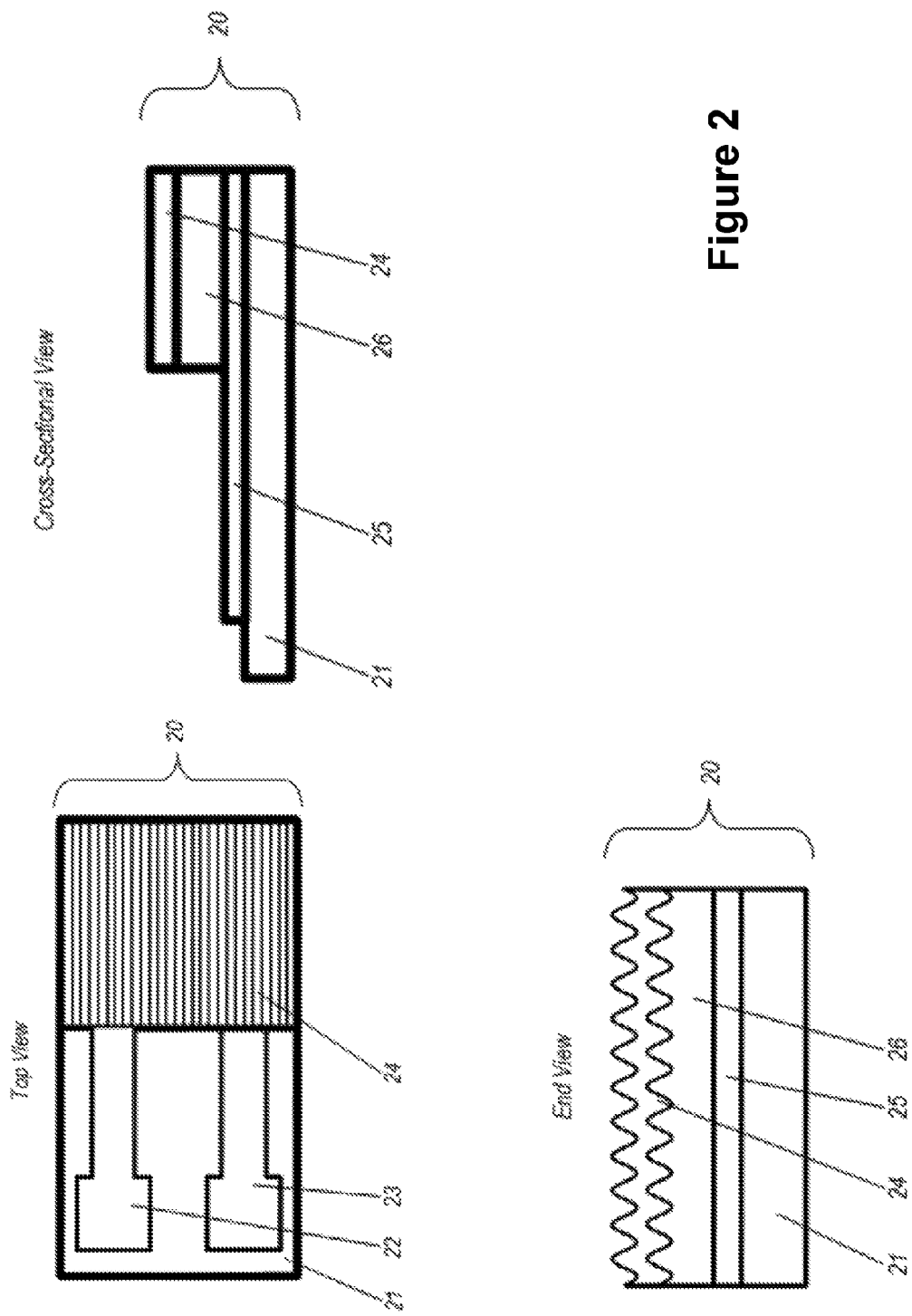

ELECTRO-OPTIC GRATING-COUPLED SURFACE PLASMON RESONANCE (EOSPR)

CROSS-REFERENCE TO RELATED APPLICATIONS

This application is a continuation of U.S. patent application Ser. No. 14/534,511, filed Nov. 6, 2014, for "Electro-Optic Grating-Coupled Surface Plasmon Resonance (EOSPR)," which claims the benefit of U.S. Provisional Patent Application No. 61/900,548, filed Nov. 6, 2013, the entire contents of each of which are hereby incorporated by reference.

STATEMENT REGARDING FEDERALLY SPONSORED RESEARCH OR DEVELOPMENT

This application is based on research and development done under NIH/NIGMS Grant No. 1R43GM104636-01.

TECHNOLOGICAL FIELD

The described embodiments relate to an instrument and method for the detection, measurement, and characterization of a wide variety of specific molecules, simple or complex solutions, and biological cells.

BACKGROUND OF THE INVENTION

Requirements for the identification and measurement of biological or chemical entities in a sample typically include a means of isolating or separating the analyte in question. Once spatially, temporally, or otherwise isolated from the surroundings, the analyte provides or promotes a signal whose intensity can be interpreted as a measure of the presence and/or concentration of analyte originally present in the sample. For example, one common approach to enzyme-linked immunosorbant assays (ELISAs) utilizes capture ligands to retain the analyte in question at the bottom of a microtiter plate while irrelevant molecules are removed from the well in a series of washes. When a fluorescently-labelled antibody targeting a second epitope is introduced, the signal from adherent fluorophores can be interpreted as proportional to the concentration of analyte present in the original sample. In this and other embodiments, absolute measurements are achieved via comparison with a parallel signal arising from a known quantity of analyte.

Surface plasmon resonance (SPR) assays are based on the coupling of P-polarized incident light to a surface plasmon wave, a physical mode created by charge density oscillations at a metal-dielectric interface. The mismatch in dielectric constants between these two materials supports a mode of evanescent electron excitation known as a surface plasmon. Coupling of the light to this mode, known as resonance, requires a momentum match between the plasmon and the incident light, and consequently is exquisitely sensitive to the properties of the light. When conditions are optimal, the majority (>90%) of the light acts to excite the plasmon, with little being reflected. Detectors placed in the optical path of reflected light are able to measure this intensity as a function of incident angle, wavelength, or phase, and instrumentation has been developed that generates intensity plots as a function of each of these variables. The nadir of the intensity plot is known as the SPR minimum, and it defines the conditions where optimal coupling into the plasmon mode occurs.

The value of the independent variable defining the SPR minimum changes with the dielectric constant at the surface, a phenomenon which underlies the utility of SPR techniques in biological or chemical sensing. Accumulating mass (e.g. protein binding) at the sensor surface leads to a proportional change in the dielectric constant, and a consequent change in the value associated with the SPR minimum. This "SPR shift" acts in a sense like a "molecular scale," providing quantitative measures of changes in mass at the sensor surface. Thus SPR acts in a sense like a "molecular scale," where change in surface mass recorded as an "SPR shift." Detection of a specific biological molecule can occur with the attachment of an appropriate capture ligand to the sensor surface, (antibodies, oligonucleotides, aptamers, etc.) serving to capture the analyte of interest present in a sample as it flows over the surface. Additional flow of buffer provides a wash sequence to remove non-specific adherents. While this approach has much in common with ELISA, a secondary antibody is not required to measure the SPR signal; the accumulation of mass is theoretically sufficient. Alas, SPR has not proven sensitive enough to detect trace quantities of small molecules, particularly in complex media, and the low sensitivity of classic approaches to SPR as compared to labeled techniques like ELISA has proven to be a limitation to the application of this technology to environmental and clinical samples.

SPR is an evanescent phenomenon and therefore the effect on the dielectric constant is limited to the region immediately surrounding the mass. Indeed in at least one instrument architecture, densities exceeding 1,000 spots/cm$^2$ have been achieved with no significant cross-talk. This opportunity for spatial separation of multiple analytes utilizing an assortment of capture ligands permits an increase in the number of experiments performed on a single chip. When spotted in a 2D array, parallel intensity measurements can be performed using a camera, with pixel clusters defined in silico around each antibody spot. These regions of interest (ROI) serve as independent assays of analytes present in the sample, with shifts in the SPR minima of each ROI providing binding kinetics and end-point concentrations.

The Kretschmann Configuration—The most common method for momentum matching between incident light and the surface plasmon mode is known as the Kretschmann configuration and is dependent on the sensor surface being in optical contact with a high-refractive index prism. Limitations of the Kretschmann configuration include instrument size, instrument price, ease of use, and the relatively small number of simultaneous analyses that can be performed. The physics of this configuration as an SPR detection scheme is well-established (see Homola, J., 2006, *"Surface Plasmon Resonance Based Sensors"*, Springer Series on Chemical Sensors and Biosensors: Methods and Applications: 1-252), but for the purpose of this disclosure one key element of the design should be noted. Kretschmann instrumentation architecture most frequently contains a single metal layer with two pertinent surface interfaces, to be known going forward as the metal-sample interface and the metal-prism interface. In this configuration, coupling is dependent not only on the dielectric constants of the metal and the sample, but also on that of the prism as can be seen in equation 1:

$$\tan(\kappa_{sp} d/2) = \frac{\gamma_1 \varepsilon_2 / \kappa \varepsilon_1 + \gamma_3 \varepsilon_2 / \kappa \varepsilon_3}{1 - (\gamma_1 \varepsilon_2 / \kappa \varepsilon_1)(\gamma_3 \varepsilon_2 / \kappa \varepsilon_3)} \quad (1)$$

where $\kappa_{sp}$ is momentum of the plasmon wave that exists on a dielectric-metal-dielectric and $\kappa^2 = \omega^2 \in_2 \in_0 \mu_0 - \beta^2$ and $\gamma_{1,3}^2 = \beta^2 - \omega_2 \in_{1,3} \in_0 \mu_0$. d is the thickness of the metal layer, $\omega$ is the angular frequency, $\in_0$ is permittivity of free space and $\in_n$ is the dielectric constant of medium n, $\mu_0$ is the free-space permeability, and $\beta$ is the propagation constant of the plasmon mode. In the Kretschmann configuration, $\in_1$ is the dielectric constant of the sample, $\in_2$ is that of the metal, and $\in_3$ is that of the prism. The metal layer is made sufficiently thin (~50 nm) that changes in the resonant conditions established by sample accumulation at the metal-sample interface are affected by the dielectric constant of the prism at the metal-prism interface. This reduced thickness permits the plasmon to "penetrate" into the prism, and allow for coupling conditions to be interrogated from the opposite side of the metal film as the sample.

Grating-coupled SPR (GCSPR)—This approach achieves momentum matching using diffracted light, often produced by means of a sensor chip with an embossed diffraction grating. This coupling scheme simplifies sample preparation, reduces instrument cost, and allows for epi-illumination optics, vastly increasing the number of assays performed simultaneously. Although detection of the SPR minimum in a GCSPR system can be readily achieved by varying angle, wavelength, or phase, this discussion will focus on an angle-scanning approach to GCSPR. Similar principles apply for these other detection modalities, but an angle-scanning approach simplifies equations and facilitates direct comparison with commercially available technologies. In these platforms, much like their Kretschmann counterparts, changes in dielectric constant due to bound mass ($\Delta \in_1$) affect $\kappa_{sp}$, while the values of $\in_2$ (the metal) and $\in_3$ (the underlying substrate) do not vary. Similarly, in GCSPR, the change in $\kappa_{sp}$ is detected by varying the incident angle ($\theta$) until the light's momentum (k-vector) matches $\kappa_{sp}$, and resonance is achieved. The equation that governs coupling into the GCSPR system is reproduced in equation 2:

$$\kappa_{source} \sin \theta + m\kappa_{grating} = \kappa_{sp}(\in_1, \in_2, \in_3) \quad (2)$$

The above shows that when $\kappa_{source}$ and $\kappa_{grating}$ are fixed, as occurs readily in classic GCSPR instruments, the mass-dependent changes in $\in_1$ shape $\kappa_{sp}$ and are observed as changes in the coupling angle ($\theta$). Local refractive index changes at the metal-dielectric interface are detected with incident light that passes through this dielectric, so in this configuration, the thickness of the metal is irrelevant, as long as it exceeds the minimum necessary to support SPR. Due to the robustness and the relative ease of manufacture, metal layers in most GCSPR platforms have been sufficiently thick (~1 µm) as to obscure any effect of $\in_3$ on the plasmon coupling conditions. While GCSPR systems offer considerable improvement over the limitations of Kretschmann systems, they remain less sensitive than fluorescent techniques, and the dependence on moving parts for angle scanning makes these instruments relatively fragile and therefore ill-suited for field use.

Surface Plasmon-Coupled Emission (SPCE)—It has been observed that energy from surface plasmons can be out-coupled and absorbed by fluorophore molecules in close proximity to the metal surface (see Lackowicz, J. R., 2006, "Plasmonics in Biology and Plasmon-Controlled Fluorescence", DOI 10.1007/s 11468-005-9002-3). The local field of the propagating wave at the metal/dielectric boundary enhances absorption of plasmons as compared to free-space absorption. The subsequent fluorescent emission is out-coupled into propagating lobes in accordance with the momentum matching conditions previously described. Fluorescence generated in this manner is emitted as directional lobes rather than omnidirectionally as in a solution (i.e., as in a typical fluorimeter). An optical detection system can be designed to capture this SPCE with much greater efficiency than can be done with omnidirectional fluorescence. This enhanced capture efficiency results in considerably greater detection sensitivity and is sufficient to quantitatively measure cytokine secretion from single cells (see Reilly, M. T., et al., 2005, "SPR surface enhanced fluorescence with a gold-coated corrugated sensor chip" Progress in Biomedical Optics and Imaging—Proceedings of SPIE Volume 6099, Article number 60990E DOI: 10.1117/12.646165).

Electro-optic polymers are polymers with non-linear optical properties, such that they change their dielectric constant and refractive index as a function of an applied electric field. Polymers displaying the Pockel's or Kerr effect in response to applied voltage have been described and are in use in high speed optical switches in the telecommunications industry. The considerable thermal, chemical, and temporal stability are a sine qua non for commercial optical switches, and this patent aims to take advantage of recent advances enabling nanoscale patterning of said polymers.

BRIEF SUMMARY OF THE INVENTION

An analytical sensor platform that facilitates the capture and detection of specific cells or molecules on the surface of an electro-optic grating-coupled surface plasmon resonance "chip" is described herein. The complete platform is comprised of a sensor chip with an integrated or stand-alone yet complementary detection apparatus supporting surface plasmon resonance and/or surface plasmon coupled emission analyses. As detailed below, one sensor chip architecture consists of an inert substrate for structural support, upon which a conductive layer is deposited, upon which a grating-embossed or otherwise patterned electro-optic polymer is deposited, and upon which a thin gold layer is placed. In this embodiment, each of the two conductive layers is in electrical contact with contact pads, which interface with a software-controlled voltage generator.

Instrumentation will consist of, at minimum, a source of polarized, collimated light suitable for achieving SPR and/or SPCE on the proposed chip. The chip will be manufactured to include or converted by the end-user into a fluid-tight enclosure known as a "flow chamber," permitting the introduction and retention of samples, buffers, or other reagents. One design forms a flow chamber by means of a gasket surrounding the active area of the chip and a transparent window sandwiching the gasket and establishing a small volume for liquids to pass over the sensor chip. Fluid inlets and outlets manifesting as small holes in the window will interface with pumps, valves, tubing, and other fluidic systems necessary to provide circulation or recirculation of sample, wash, or other fluid over the active area of the sensor chip. Optics will act to isolate signal from noise and project emitted light onto a director surface (e.g. camera, photodiode array), and when measuring SPCE, direct incident light away from the detector, maximizing the contribution of fluorescent emission to the signal. Computer software will permit the manual or automated control of optics, fluidics, and voltage; and will also assist with data collection, manipulation, analyses, and presentation.

The EOSPR chips will present development challenges, and we seek to describe herein one method of chip manufacture. Briefly and as envisioned, this manufacturing effort will consist of deposition of a conductive material onto a structural support platform, positioned below what will become the active area of the chip, with a small extension facilitating electrical interfacing with this layer. Overlying this layer, at the active area of the chip, will be a layer of EO material whose dielectric and optical properties vary with the strength of an electric field applied to the EO material. One example of an EO material is a poled EO polymer patterned to form a diffraction grating. Two potential approaches to this step are presented below to illustrate the general concept. The first will deposit the polymer as a uniform layer, poling the polymer as it relaxes below its glass temperature. The grating structure will subsequently be generated directly in the polymer using lithographic patterning techniques. The latter approach will emboss hot polymer with a metal shim containing a complementary diffraction grating pattern. One example of an EO polymer material compatible with the disclosed EOSPR chips is SEO100 electro-optic polymer from Soluxra, LLC of Seattle, Wash.

In one disclose example, poling will occur as the polymer cools with an electric field applied between the "stamp" and the lower conductive layer of the chip. In either case, an SPR-active material is deposited on top of the grating. The most common SPR-active materials are metals with free electrons available for coupling into surface plasmons propagating along the surface of the metal. The SPR active metal will be deposited atop the grating as a thin layer, and will also extend to a blank region of the chip to facilitate the application of a voltage between the two conductive layers sandwiching the EO polymer to establish an electric field in the EO polymer.

As with many other SPR platforms, the variable representing the accumulation of mass at the sensor surface is the SPR minimum of reflected intensity at individual ROIs. Unlike most other SPR platforms, electro-optic surface plasmon resonance observes the intensity modulations defining an SPR minimum as a function of a voltage applied across an electro-optic polymer. The notion of an electro-optic approach to SPR is not without precedent; cf. U.S. Pat. Nos. 6,667,807, 8,009,356, but the novelty and advantages of the claimed detection schema absolutely require the combination of this technology with a grating-coupled approach to SPR.

BRIEF DESCRIPTION OF THE SEVERAL VIEWS OF THE DRAWINGS

FIG. 2 shows several views of one possible EOSPR chip.

DETAILED DESCRIPTION OF THE INVENTION

Figure 1:
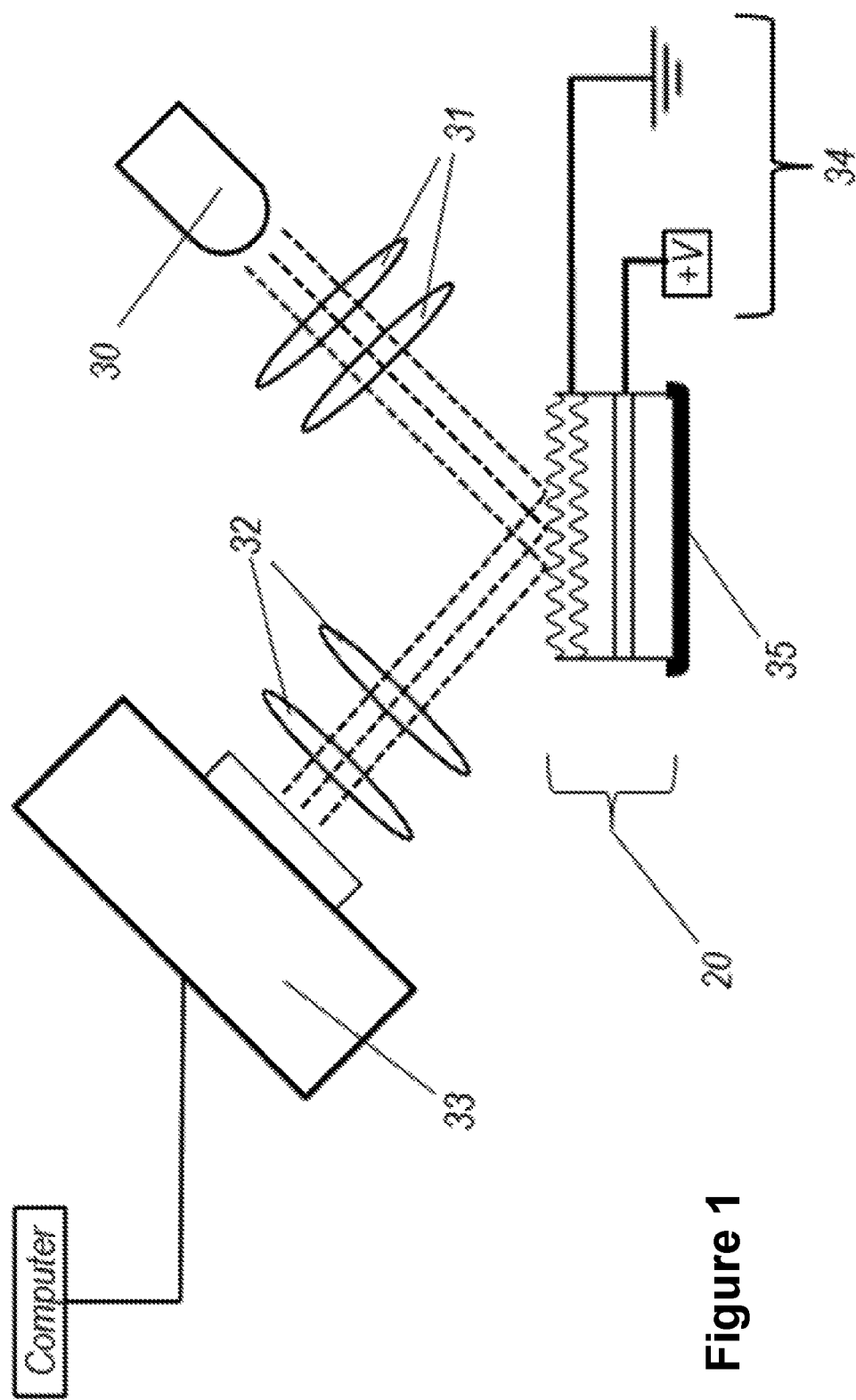
FIG. 1 is a schematic drawing showing one possible optical path for the instrument.

As used herein, the term "electro-optic polymer" or "EO polymer" refers to polymers or other materials whose dielectric constant varies as a function of applied voltage. SEO100 from Soluxra, LLC of Seattle, Wash. is an example of an electro-optic polymer potentially compatible with the disclosed embodiments. The acronym GCSPR stands for Grating-Coupled Surface Plasmon Resonance, and EOSPR stands for Electro-Optic grating-coupled Surface Plasmon Resonance. SPCE stands for Surface Plasmon Coupled Emission. The EOSPR sensor surface is alternatively called the "chip," the "sensor chip," or the "EOSPR chip," and will support an electro-optic grating-coupled approach to both SPR and SPCE.

An EOSPR sensor chip and complementary detection schema providing surface plasmon resonance analysis with or without concomitant SPCE measurements are described below.

In a dielectric-metal-dielectric arrangement, Equation 1 holds true, and $\kappa_{sp}$ therefore depends on the dielectric constant of all three layers ($\in_1$, $\in_2$, and $\in_3$). In the Kretschmann configuration, local changes in the dielectric constant due to bound mass ($\Delta\in_1$) affect $\kappa_{sp}$ while the values of $\in_2$ and $\in_3$ do not vary. The change in $\kappa_{sp}$ in these instruments is detected by adjusting the momentum of the source light, often by varying the incident angle ($\theta$) until resonance is achieved. In the grating-coupled approach, coupling into the GCSPR system is governed by Equation 2. When $\kappa_{source}$ and $\kappa_{grating}$ are fixed, as occurs readily in classic GCSPR instruments, the mass-dependent changes in $\in_1$ shape $\kappa_{sp}$ and are observed as changes in the coupling angle ($\theta$). Equations that define $\kappa_{sp}$ and the coupling angle $\theta$ for Kretschmann instruments are similar. However, the EOSPR platform departs from these detection schema by restricting $\theta$ to a given angle (e.g. the SPR angle for a water-gold-plastic construct), or a small range of angles and instead interrogating accumulation or depletion of bound mass by changing $\in_3$. To clarify, one approach to detection would measure the effect of accumulating mass (manifesting $\Delta\in_1$) not by changing the properties of the incident light (e.g. angle), but instead by changing the properties of the underlying grating itself ($\Delta\in_3$). As alluded to above, classic GCSPR instruments are not thought of as dielectric-metal-dielectric systems because the metal layer is typically thick enough to obscure any impact of $\in_3$. For $\in_3$ to be relevant, as is proposed in this EOSPR approach, the thickness of the metal layer must be reduced to thicknesses such as those found in Kretschmann e.g., less than approximately 50 nm. In this case, the controlled change in $\in_3$ will be accomplished by replacing the underlying dielectric with a polymer displaying a significant electro-optic (EO) effect.

Integrating an EO polymer into a GCSPR-style chip permits a detection scheme where departures from resonant conditions ($\Delta\in_1$) will be measured solely by varying the dielectric constant of the EO polymer. The dielectric constant change at the surface due to binding mass (typically no larger than ~$10^{-5}$ RIU) is readily matched by changes in the dielectric constant of the polymer (which can modulate by as much as $10^{-3}$ RIU). The precise match between incident light and the plasmon mode would therefore not be a function of angle, but a function of applied voltage.

One embodiment of the EOSPR chip (20) is sketched as FIG. 2, the components of which are built upon an inert substrate (21). Above this substrate is a conductive layer (25) whose properties support the application of voltage and adhesion of the polymer layer (26). This conductive layer need not be metal nor SPR active, but along with the SPR-active metal surface (24) acts to promote the application of a uniform electric field across the EO material. The EO material (26) is a layer that has been patterned to act as a diffraction grating, but whose optical properties continue to display a significant electro-optic effect. An SPR-active metal surface (24) overlies this particular embodiment, and contact pads (22 and 23) are continuous with the two conductive layers (24 & 25).

The instrumentation portion is presented here as a stand-alone device interfacing with the EOSPR chip, providing control of input voltage, monitoring reflected light intensity at the sensor surface, controlling fluidics, and interpreting data. Devices offering any and all of these functionalies in a package designed to support this grating-coupled electro-optic approach to SPR or SPCE sensing shall comprise an "EOSPR instrument" for the purposes of this discussion. As presented, the minimum components for such a system include a light source (30), a polarizer and collimated lens (31), the chip (20, perhaps positioned on a removable holding apparatus, 35), suitable filters and lenses (32), a detector (33), the voltage generator (34), and a computer. Fluidics, their interfaces, and controls may be a component of the chip, a component of the instrument, or may stand alone, but are not represented in the figures for clarity.

The archetypal detection scheme proposed herein involves optimizing the instrument so that the incident angle and the detector (camera, photo-diode array, etc.) are fixed at approximately the SPR angle for the bare gold surface. Room for adjustment of this angle can be engineered into the design, permitting user calibration and/or increased instrument tolerance for varied environmental conditions. Instead of monitoring reflected intensity as a function of incident angle, the instrument would measure reflected intensity as a function of voltage applied to the bottom electrode. In the most straightforward scanning protocol, the incident angle and the location of the light detector will not move. Since electro-optic polymers change dielectric constant predictably in the presence of an electric field, applying a voltage to this basal electrode while maintaining the surface metal at ground would generate a change in the dielectric constant of the sandwiched polymer ($\Delta\epsilon_3$). With the surface grounded, interference with biological interactions is not expected. The assay would monitor the binding of mass to the surface by measuring the voltage required to return all ROI to resonance or a reference value. The changes in local dielectric constant imparted by the bound mass on the surface would be in essence nullified by changes in the dielectric constant in the polymer layer. Several related works appear in the literature (including prior art from Ciencia), but none appear as well suited for commercial adoption as the EOSPR platform, primarily due to the epi-illumination architecture.

The addition of an electro-optic layer in between conductive layers adds slight complexity to the chip, yet greatly reduces the requirements for instrumentation. The EOSPR chip eliminates the need for moving parts and significantly shortens the optical pathway. The proposed device would be able to simultaneously measure the shifts for the same number of ROI ($\sim$1,000/cm$^2$) as allowed by extant GCSPR instrumentation. The number of spots is constrained by the active area of the chip, since the density of spots is limited to prevent an overlap of plasmon waves. There is no fundamental reason why smaller or larger chips with tens or millions of spots could not be developed for future instruments. In any implementation, the reduced weight, cost, and fragility would make EOSPR instrumentation more portable and affordable, while increasing sensitivity over comparable GCSPR platforms. By selecting small components and a smaller chip (active area of $\sim$4 mm$\times$4 mm, enough for $\sim$100 spots) we have calculated that an optimized and sensitive EOSPR instrument could be about the size and weight of an average hardcover novel. Bringing a sensitive and high-content assay into the realm of hand-held and battery-operated devices invites enticing market opportunities.

Although it is hard to quantify the sensitivity increase expected from this design ab initio, several factors inherent to this system imply that the inclusion of EO polymers will boost instrument performance beyond today's standards. Implicit in the EOSPR design are increases in the quality of the signal and decreases in the noise compared to other SPR platforms. Applied voltage can be measured more accurately than the mechanical changes of incident angle present in current systems, thus locating the SPR with high precision. In addition, thousands of measurements defining the SPR minimum could be conducted in the time it takes to perform a single scan on current instrumentation. This increased scanning velocity would also permit direct measure of faster reaction kinetics. Finally, voltages could be applied in a pseudo-random fashion with collected data interpreted in silico, thus reducing systematic error in measurements.

Besides boosting the quality of the signal, direct reduction of instrument noise is possible with such a rapidly scanning instrument. Even with an inexpensive 30 Hz camera, we can employ a signal-chopping scheme to subtract noise as background. Essentially, the voltage applied to the EO material would switch from a near-resonant voltage to an off-resonant voltage at a rate of 30 Hz synchronized to the camera. The near-resonant image provides the signal, while the off-resonant image provides the background. The difference between these two images would be immune to many sources of noise, such as stray light, changes in temperature, changes in light intensity, etc. For a 30 Hz frame rate, 15 background subtracted images can be obtained per second, still allowing for extensive averaging at a reasonable data acquisition rate. The enhanced quantities of high-quality data collected by the electronic detection scheme and the expected reduction of noise encountered by chopping the signal combine to strongly suggest an overall increase in instrument sensitivity. High-sensitivity measurements and a compact, stable, and no-moving-parts design strongly suggest this platform would be ideal for field use.

What is claimed is:

1. An instrument for detecting changes in the optical properties of a sensor surface defining an image plane, said instrument comprising:
    an electro-optic material having a surface including a diffraction grating coincident with said image plane, said electro-optic material having a dielectric constant and refractive index that change as a function of the strength of an electric-field to which the electro-optic material is exposed;
    an SPR-active layer on said diffraction grating;
    a voltage generator arranged to deliver a variable voltage to said electro-optic polymer, thereby exposing said electro-optic material to a variable electric field which changes the dielectric constant and refractive index of said electro-optic material;
    a source of collimated polarized light of a predetermined wavelength arranged to project said collimated polarized light onto said image plane at a defined angle of incidence;
    an imaging detector arranged to form an image of said sensor surface from said polarized light reflected from said sensor surface;
    wherein at least a portion of said polarized light is coupled into surface plasmons at said sensor surface and the intensity of the reflected light received by said imaging detector varies as a function of the intensity of said electric field.

2. The instrument of claim 1, wherein said electro-optic material, diffraction grating, SPR-active layer, and predetermined wavelength result in a resonant angle at which a majority of the polarized light is coupled into surface plasmons at said SPR-active layer and said resonant angle changes as a function of the strength of said electric field.

3. The instrument of claim 2, wherein said resonant angle changes in response to a mass of material bound to said SPR-active layer, the applied voltage can be varied to change the strength of said electric field to correct for changes in said resonant angle due to material bound to said SPR-active layer and the change in voltage can be used to measure said mass of material bound to said SPR-active surface.

4. A method of measuring changes in the optical properties at a sensor surface defining an image plane comprising the steps of:
providing an electro-optic material with a conductive layer on one side and a diffraction grating opposite the conductive layer and an SPR-active layer on said diffraction grating forming said sensor surface, said electro-optic material having a dielectric constant and refractive index that vary as a function of an electric field established between said conductive layer and said SPR-active layer;
connecting a variable voltage generator to said conductive layer and said SPR-active layer;
arranging a source of collimated polarized light of a predetermined wavelength to project said collimated polarized light onto said sensor surface at a defined angle of incidence;
positioning an image detector to form an image of said sensor surface from said polarized light reflected from said sensor surface;
monitoring the reflected intensity as a function of a variable voltage applied across said conductive layer and said SPR-active layer.

5. The method of claim 4, comprising:
establishing a reference image of said sensor surface at a first voltage applied across said EO material;
causing material to bind to said sensor surface, thereby altering the optical properties of the sensor surface; and
varying the voltage applied across said EO material to re-establish said reference image at a second voltage; and
employing a change in voltage between said first voltage and said second voltage to determine the mass of material bound to said sensor surface.

6. The method of claim 4, wherein said step of connecting a variable voltage generator comprises connecting said SPR-active layer to ground.

* * * * *